(12) United States Patent
Nanjo et al.

(10) Patent No.: US 10,514,334 B2
(45) Date of Patent: Dec. 24, 2019

(54) CELL MEASUREMENT METHOD

(71) Applicant: Kurashiki Boseki Kabushiki Kaisha, Okayama (JP)

(72) Inventors: Yuko Nanjo, Osaka (JP); Hiroyuki Asano, Osaka (JP); Isao Miyagawa, Osaka (JP); Yoshio Takada, Osaka (JP)

(73) Assignee: Kurashiki Boseki Kabushiki Kaisha, Okayama (JP)

( * ) Notice: Subject to any disclaimer, the term of this patent is extended or adjusted under 35 U.S.C. 154(b) by 40 days.

(21) Appl. No.: 15/754,291

(22) PCT Filed: Aug. 17, 2016

(86) PCT No.: PCT/JP2016/073996
§ 371 (c)(1),
(2) Date: Feb. 21, 2018

(87) PCT Pub. No.: WO2017/033809
PCT Pub. Date: Mar. 2, 2017

(65) Prior Publication Data
US 2018/0252636 A1 Sep. 6, 2018

(30) Foreign Application Priority Data
Aug. 26, 2015 (JP) ................................. 2015-167122

(51) Int. Cl.
*G01N 21/27* (2006.01)
*C12M 1/34* (2006.01)
(Continued)

(52) U.S. Cl.
CPC ........... *G01N 21/27* (2013.01); *C12M 1/3461* (2013.01); *C12M 1/3476* (2013.01); *C12Q 1/06* (2013.01);
(Continued)

(58) Field of Classification Search
CPC . G01N 21/27; G01N 21/8806; C12M 1/3461; C12M 41/36
See application file for complete search history.

(56) References Cited

U.S. PATENT DOCUMENTS 3,327,117 A * 6/1967 Kamentsky ............ A61B 10/00
250/373
5,356,793 A 10/1994 Koezuka et al.
(Continued)

FOREIGN PATENT DOCUMENTS

JP S61226638 10/1986
JP H03285696 12/1991
(Continued)

OTHER PUBLICATIONS

"International Search Report (Form PCT/ISA/210) of PCT/JP2016/073996" dated Oct. 11, 2016, with English translation thereof, pp. 1-4.

*Primary Examiner* — Kim Y Vu
*Assistant Examiner* — Molly Delaney
(74) *Attorney, Agent, or Firm* — JCIPRNET

(57) ABSTRACT

To show a highly accurate cell measurement method. A cell measurement method comprises: a step of staining a cultured target cell with a dye; a step of obtaining a first image and a second image which are transmission images for a first light and a second light to which the dye has different absorbance; a step of dividing each of the first image and the second image into a plurality of divided regions and comparing the first image and the second image for each of the divided regions so as to eliminate noises; and a step of integrating an indicator of a cell amount in each of the divided regions in the images from which the noises were eliminated so as to evaluate a target cell amount.

13 Claims, 5 Drawing Sheets

(51) Int. Cl.
*G01N 21/88* (2006.01)
*G01N 33/483* (2006.01)
*G01N 21/17* (2006.01)
*C12Q 1/06* (2006.01)

(52) U.S. Cl.
CPC ..... *G01N 21/8806* (2013.01); *G01N 33/4833* (2013.01); *G01N 2021/1734* (2013.01)

(56) References Cited

U.S. PATENT DOCUMENTS

| | | | |
|---|---|---|---|
| 5,712,161 A | 1/1998 | Koezuka et al. | |
| 7,758,811 B2* | 7/2010 | Durack | C12N 5/0612 422/73 |
| 8,129,105 B2* | 3/2012 | Zuckerman | A61B 5/14546 435/4 |
| 8,765,464 B2 | 7/2014 | Minamigawa et al. | |
| 9,310,287 B2* | 4/2016 | Medoro | G01N 15/14 |
| 10,018,640 B2* | 7/2018 | Bornheimer | G01J 3/42 |
| 10,140,547 B2* | 11/2018 | Im | G01N 21/6456 |
| 2011/0033887 A1* | 2/2011 | Fang | B01L 3/502707 435/41 |
| 2018/0360299 A1* | 12/2018 | Kishima | G02B 27/1013 |

FOREIGN PATENT DOCUMENTS

| | | |
|---|---|---|
| JP | H10115612 | 5/1998 |
| JP | 2000131322 | 5/2000 |
| JP | 3363445 | 1/2003 |
| JP | 2003222624 | 8/2003 |
| JP | 2005513502 | 5/2005 |
| JP | 2008011797 | 1/2008 |
| JP | 2014517263 | 7/2014 |
| WO | 9518216 | 7/1995 |
| WO | 03056327 | 7/2003 |
| WO | 2012142496 | 10/2012 |

* cited by examiner

CELL MEASUREMENT METHOD

CROSS-REFERENCE TO RELATED APPLICATION

This application is a 371 application of the international PCT application serial no. PCT/JP2016/073996, filed on Aug. 17, 2016, which claims the priority benefit of Japan application no. 2015-167122, filed on Aug. 26, 2015. The entirety of each of the above-mentioned patent applications is hereby incorporated by reference herein and made a part of this specification.

TECHNICAL FIELD

The present invention relates to a method for measuring a cell amount.

BACKGROUND ART

In a susceptibility test for an anticancer agent against epithelial malignant tumor, sarcoma, etc., a cancer cell brought into contact with an anticancer agent and a cancer cell not brought into contact with the anticancer agent are cultured under the same condition, and the proliferation degrees of the cancer cells after cultivation are compared so as to evaluate susceptibilities of the cancer cells to the anticancer agent. The less proliferation of the cancer cell is, the better the anticancer agent is.

As a method for culturing cancer cells, Patent Documents 1 to 5 describe methods for culturing cancer cells by embedding them in a collagen gel. This collagen gel embedding cultivation is known to proliferate cancer cells better compared to a surface cultivation in which cancer cells are cultured on a surface of agar or the like.

As a method for quantitating a cultured cancer cell, Patent Document 1 describes a method in which a proliferated cancer cell is imaged with a TV camera or the like, and then obtained image information is electronically image-analyzed to calculate estimated volume values of cancer cell colonies. In addition, Patent Document 3 describes a method in which a cancer cell cultured in a collagen gel is stained with a dye, imaged, and quantitated based on an image density.

PRIOR ART DOCUMENTS

Patent Documents

Patent Document 1: JP H03-285696 A
Patent Document 2: WO 95/18216
Patent Document 3: JP H10-115612 A
Patent Document 4: JP Pat. No. 3363445
Patent Document 5: JP 2008-11797 A

SUMMARY OF INVENTION

Problem to be Solved

The cancer cell quantitating methods described in Patent Document 1 and Patent Document 3 had problems of further improvement for quantitative precision. The susceptibility tests to anticancer agents have been conventionally performed using surgical materials taken from cancer patients as starting materials. In recent years, there has been growing demand for an anticancer agent susceptibility test using a biopsy material as a starting material, in which cells are sampled with a puncture needle or the like for the purpose of reducing physical burden of a patient. However, for the biopsy material, since tissue pieces that can be sampled are smaller than surgical materials, it is required in the anticancer agent susceptibility test to precisely quantitate less than or equal to one-tenth cell amount of that in the conventional test. In Patent Document 1 and Patent Document 3, it was difficult to precisely quantitate such a small amount of cancer cell.

The present invention has been made in view of the above circumstance, and the present invention provides a cell measurement method with higher quantitative precision.

Solution to Problem

The cell measurement method of the present invention comprises: a step of staining a cultured target cell with a dye; a step of obtaining a first image and a second image which are transmission images for a first light and a second light to which the dye has different absorbance; a step of dividing each of the first image and the second image into a plurality of divided regions and comparing the first image and the second image for each of the divided regions so as to eliminate noises; and a step of integrating an indicator of a cell amount in each of the divided regions in the images from which the noises were eliminated so as to evaluate a target cell amount.

Herein, the target cell means a cell to be measured. In addition, the noise means unnecessary image information not derived from the stained target cell. Furthermore, the indicator of the cell amount means an indicator which increases or decreases depending on the amount of the cell, such as a density of the image or an absorbance calculated from the density of the image. This method eliminates the influence of the noises resulting in errors, so that the cell amount can be precisely measured.

Preferably, in the step of eliminating the noises, the first image and the second image are compared for each of the divided regions, and when a difference or a ratio of luminosity between the divided regions subjected to the comparison is less than a predetermined value, the divided regions are excluded from the data as a basis for evaluation of the target cell amount.

Alternatively, preferably, in the step of eliminating the noises, the first image and the second image are compared for each of the divided regions, and when a difference or a ratio of absorbance between the divided regions subjected to the comparison is less than a predetermined value, the divided regions are excluded from the data as a basis for evaluation of the target cell amount.

Preferably, the target cell is a cancer cell.

Preferably, the target cell is a three-dimensionally cultured cell, and more preferably a cell cultured by embedding the cell in a collagen gel.

Preferably, the first image and the second image are obtained by color-separating an image taken using one color camera while concurrently applying the first light and the second light.

Alternatively, preferably, the first image and the second image are obtained by independently taking each image using one camera while sequentially applying the first light and the second light Preferably, the target cell amount is evaluated by calculating an absorbance from the image luminosity for each of the divided regions, and integrating the obtained absorbance over the plurality of divided regions to calculate an estimated volume value of the target cell.

Effects of Invention

According to the cell measurement method of the present invention, the cell amount can be precisely evaluated even when the amount of the cultured target cell is small.

DETAILED DESCRIPTION OF EMBODIMENTS

As a first embodiment of the cell measurement method of the present invention, a method of quantitating a cancer cell in an anticancer agent susceptibility test will be described below.

Prior to the cultivation, tissues sampled from a living body are subjected to dispersion treatment such as chopping and digestion of intercellular substances by a cell dispersion enzyme treatment. In some cases, separation treatment is subsequently carried out in which unnecessary cells such as blood is removed by preliminary cultivation and living cells are collected.

Various known methods can be used to prepare a cultured sample. Above all, a three-dimensional cultivation is preferably used. More preferably, a collagen gel embedding cultivation is used. This method allows preferable cultivation and subsequent quantitation of the cancer cell even when the amount of the cancer cell used for cultivation is small.

The procedure according to the collagen gel embedding cultivation is as follows. A separated and dispersed cell is blended into a collagen solution. At this time, besides collagen, various components necessary for cultivation can be added to the collagen solution. For example, a buffer solution which is the same as or similar to the physiological condition of the target cell can be added to the collagen solution. The collagen solution containing the cancer cell is dropped onto the supporting surface in the culture container to form a collagen gel in a form of droplet, and the liquid medium is added into the culture container. Similarly, several samples are prepared. For some samples, an anticancer agent is added to the culture container, and after a predetermined time, the anticancer agent is washed away, and cultivation is carried out again.

After completion of the cultivation, a dye is added to the culture container to stain the cancer cell as a target cell. As a staining method, a staining method in conventional cancer cell cultivation can be applied. Specific examples include a Giemsa solution dyeing method, a crystal violet dyeing method, a neutral red (NR) dyeing method, a fluorescein diacetate (FDA) dyeing method, and dyeing methods using other fluorescent reagents. As a staining method, a method in which cancer cells can be selectively stained and components other than cancer cells are stained as little as possible, is preferable. Use of a living cell-staining method for selectively staining a living cell is suitable for measuring susceptibility to an anticancer agent, or the like. The NR staining method is preferable as a method capable of selectively staining only living cells among cancer cells.

After completion of staining, the dye is fixed within the cell with formalin and dried. In the dried collagen gel, moisture is released from the droplet-like collagen gel, so that the gel is in a form of flat face.

Figure 2:
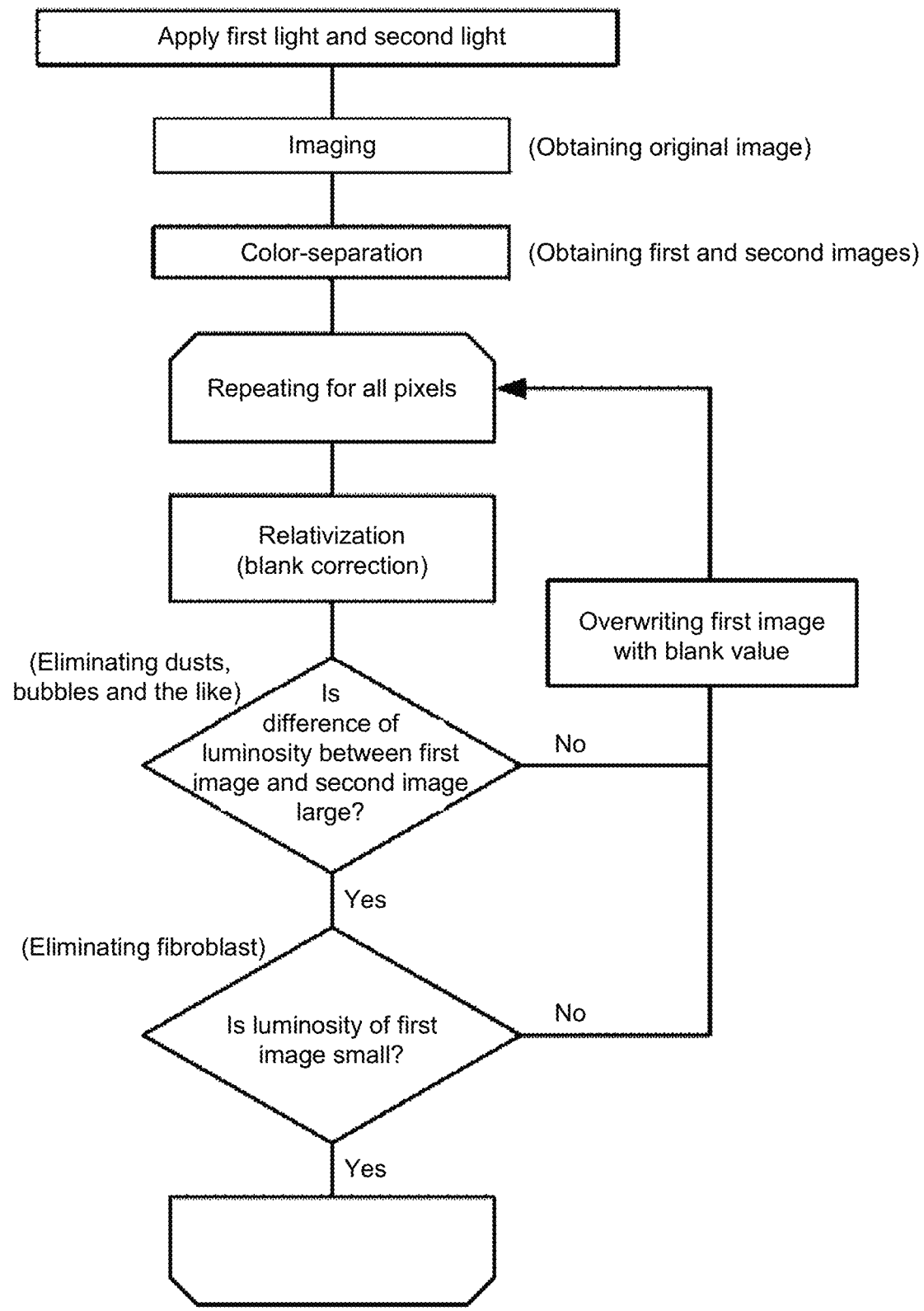
FIG. 2 is a flow chart of a cancer cell quantitating method according to the first embodiment of the present invention.

Next, a method for imaging a sample including a target cell and processing the image will be described. A flowchart of the process is shown in FIG. 2.

Figure 1:
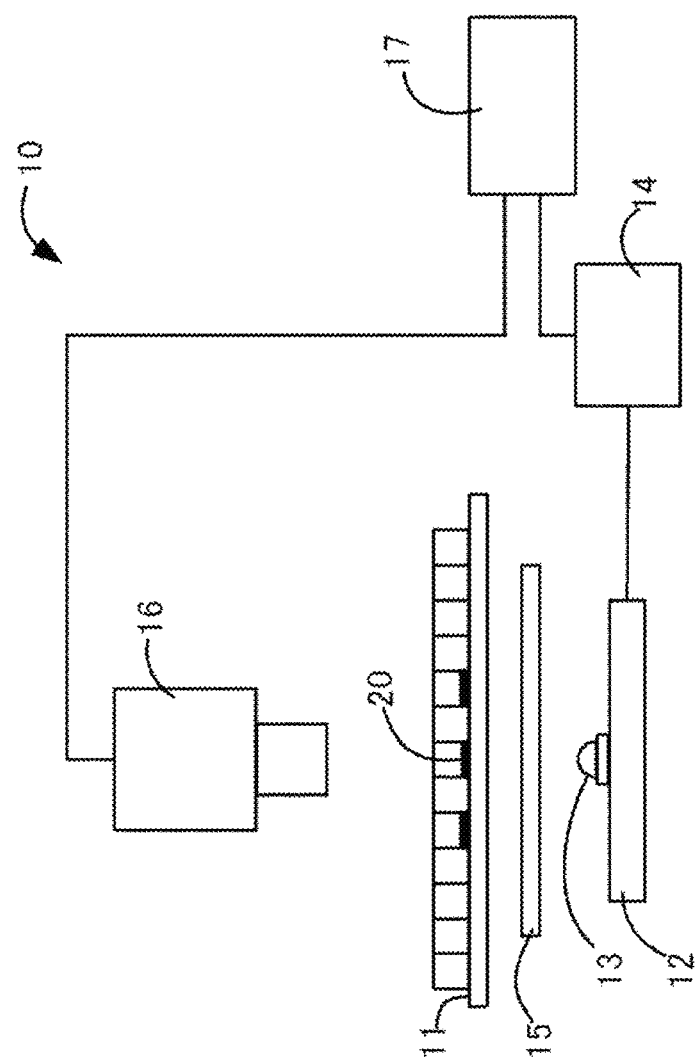
FIG. 1 shows a configuration example of a cell measuring apparatus used in a first embodiment of the present invention.

In FIG. 1, a measuring apparatus 10 according to the present embodiment comprises: a sample stage 11 on which a sample 20 is placed; an illumination 12 for illuminating the sample from below; a color camera 16 for imaging a transmission image of the sample; and an image processor 17. The illumination 12 comprises one LED package 13 and is connected to the illumination power supply 14. A light diffusion plate 15 is inserted between the illumination and the sample stage. In each LED package, an LED chip for emitting first light (not shown) and an LED chip for emitting second light (not shown) are incorporated.

Between the first light and the second light, there is a difference in absorbance by the dye which has stained the sample. In the present embodiment, the first light and the second light are concurrently applied to the sample, and the sample is imaged by one color camera to obtain one original image. This original image is color-separated, so that a first image as a transmission image for the first light and a second image as a transmission image for the second light can be obtained.

For the first light and the second light, it is preferable that the difference in absorbance by the dye therebetween is greater. In order to obtain sufficient measurement precision, a ratio of transmission loss between the first light and the second light in transmitting through the sample is preferably 1:1.5 or more, more preferably 1:2 or more. For that purpose, the difference in absorbance therebetween is preferably log $1.5 \approx 0.18$ or more, more preferably log $2 \approx 0.30$ or more. Since the absorbance varies depending on the measurement conditions, it is preferable to select wavelengths of the first light and the second light such that such a difference can be obtained under actual measurement conditions.

Figure 5:
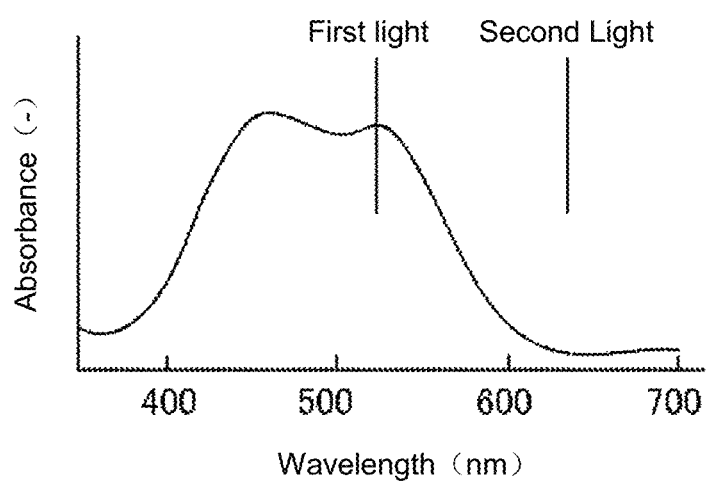
FIG. 5 shows an absorption spectrum of a neutral red.

For example, FIG. 5 shows absorption spectrum of neutral red (NR) at pH=7.1 (made from: Rika Obata et al, "Neutralization titration, and visible absorption spectrum of acid-base indicator", The Hiyoshi review of Natural Science, Keio University, No. 50, pp. 77-102, September 2011). The NR has an absorption band in a range of about 380 nm to 600 nm at this pH, and has an absorption peak at 462 nm and 518 nm. In this case, green light whose wavelength distribution overlaps with this absorption band can be selected for the first light, and red light whose wavelength distribution does not overlap with this absorption band can be selected for the second light.

As a light source for illumination, an LED is preferably used. This is because the wavelength distribution of LED is narrow and a difference between the first image and the second image is easy to clearly appear. Note that the physical form of illumination is not particularly limited. For example, the number of LED packages is not particularly limited. In addition, for example, an LED chip emitting the first light and an LED chip emitting the second light may be incorporated in one LED package as in the present embodiment, or an LED package emitting the first light and an LED package emitting the second light may be alternately arranged.

An image is constituted as an aggregate of many pixel data. Each pixel includes information representing a luminosity corresponding to a light intensity captured by image sensor elements of the camera. For example, if a gradation for inputting images is 8-bit gradation, the luminosity is represented by 256 different values from 0 to 255. If light is absorbed when transmitting through the sample, the relevant portion is dark on the transmission image, that is, the luminosity is low.

In the first image which is a transmission image for the first light, absorption by the NR is large, and thus if there are cancer cells stained with the NR in the cultured sample, the intensity of the transmitted light on the relevant portion is low. In addition, the larger the thickness of the cancer cell is, the lower the intensity of the transmitted light is, and the lower the luminosity of the image is. On the other hand, the second image which is a transmission image for the second light does not significantly reflect the presence amount of the cancer cells.

Herein, each of the first image and the second image is divided into a plurality of divided regions by the same method. The division by the same method means that a divided region of the first image and a corresponding divided region of the second image are the same in size, and imaged on the same place of the sample. The image processing described below is carried out in each of the divided regions. In the present embodiment, one pixel is defined as one divided region. Since the first image and the second image are obtained from one original image, each pixel is a region obtained by dividing both images by the same method.

Figure 3:
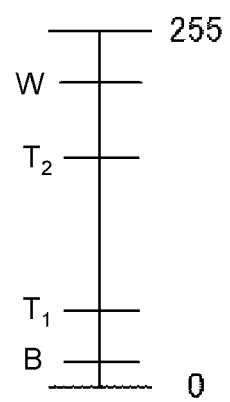
FIG. 3 is a diagram for explaining the luminosity of the image.

First, a blank image luminosity W obtained from image information of a sample containing no cancer cell is defined as an upper limit, and a dark image luminosity B obtained from image information in a dark state is defined as a lower limit, and relative values of the luminosity with respect to the upper and lower limit values are determined for each pixel to correct the first image and the second image. A blank image is an image in the brightest state obtained by imaging a blank sample treated through the same process as for the cultured sample of the cancer cell except that the cancer cell is not added. However, the blank image is not a complete white image because of the presence of a collagen gel matrix and the like. A dark image is an image in the darkest state in which light is prevented from entering by closure of a shutter of an imaging lens or the like. As shown in FIG. 3, the luminosity $T_1$ of the first image and the luminosity $T_2$ of the second image are between the luminosity W of the blank image and the luminosity B of the dark image.

Next, influence of noises is eliminated by comparing the first image and the second image.

Respective pixels are compared between the first image and the second image. If the difference or the ratio of the luminosity is less than a predetermined threshold value, the region of the relevant pixel is judged to have no cancer cell, and the pixel is excluded. In more detail, the data of the pixel is excluded from the data which is the basis for evaluating the cancer cell amount later. Specifically, for example, the first image is corrected so that the luminosity of the pixel is overwritten with the luminosity of the blank image. Thereby, the luminosity of the pixel does not affect the evaluation of the cancer cell amount and is substantially excluded.

When the difference in luminosity is defined as a reference for the threshold value, for example the threshold value can be set to one eighth of the gradation number of luminosity. That is, in a case that the luminosity is represented by 8 hits/256 grades, when the difference in luminosity between the first image and the second image is smaller than 32, the relevant pixel is excluded. Alternatively, in a case that the ratio of the luminosity is defined as a reference, when the ratio in luminosity between the first image and the second image is lower than a predetermined threshold value, it had better exclude the relevant pixel. More preferably, these threshold values are previously determined by a preliminary experiment.

Alternatively, when an absorbance is determined from the luminosity of each pixel and the difference or the ratio of the absorbance is less than a predetermined threshold value, the region of the relevant pixel may be judged to have no cancer cell.

Since opaque dusts do not transmit light regardless of the wavelength, it looks dark similarly in both the first image and the second image. In addition, since bubbles contained in the dried collagen gel look dark on the image due to light refraction, the bubbles also look dark similarly in both the first image and the second image regardless of the wavelength of the light source. Consequently, these noises can be eliminated by excluding regions where there is no difference in luminosity between the first image and the second image.

Note that bubbles are particularly problematic when the cell amount is small in collagen gel embedding cultivation. If the cell amount is small, bubbles may remain in the dried collagen gel. Although the reason is unclear, it is considered that when the cell amount is large, a gas in the gel passes through the interface between the cell and the matrix in the gel droplet mass to exit outside, whereas when the cell amount is small, the gas in the gel does not thoroughly exit but remains.

Figure 4:
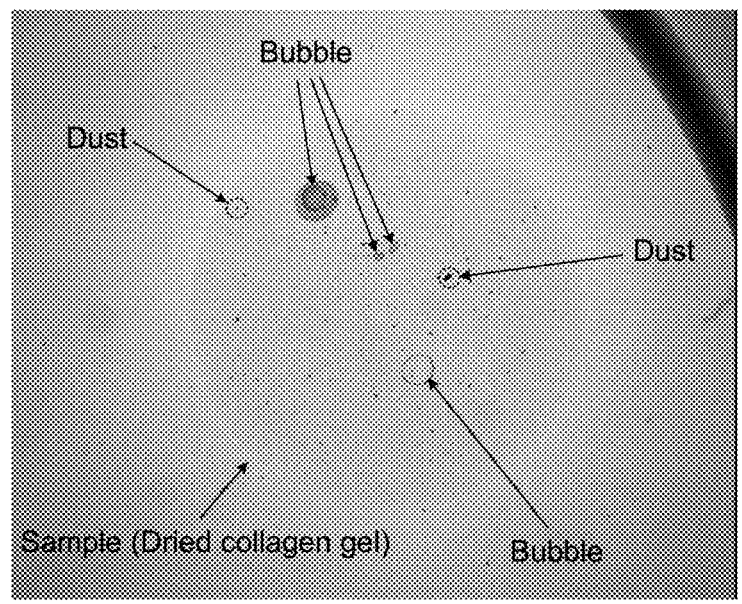
FIG. 4 is a picture for explaining an original image obtained by the cancer cell quantitating method according to the first embodiment of the present invention.

FIG. 4 shows a transmission image (original image) of a sample stained with NR. The first light was green light with a dominant wavelength of 528 nm and the second light was red light with a dominant wavelength of 625 nm. Note that FIG. 4 is a picture obtained by converting the color original image into a monochrome image, in which the resolution is also converted. The circular area at the center is the sample (dried collagen gel). Many fine dark spots scattered on the sample are cancer cells or colonies thereof, which are red in the original image, dark in the first image, and do not appear in the second image. Note that the dark spots surrounded by the dotted line are dusts, which are gray in the original image, and dark in the first image and the second image. The upper solid ellipse and the lower hollow ellipse indicate noises due to bubbles, which are gray in the original image and dark in the first image and the second image.

Another cause of noise is contamination of a fibroblast. The influence of the fibroblast can be eliminated by the method described in Patent Document 3. The fibroblast is stained with a dye such as NR together with the cancer cell, but the fibroblast is much more difficult to stain than the cancer cell, and its luminosity in the image is obviously higher than that of the cancer cell. Thus, when the luminosity of a pixel exceeds a predetermined threshold value in the first image, the region of the relevant pixel is judged to have the fibroblast, and the pixel is excluded. Specifically, for example, the first image is corrected so that the luminosity of the pixel is overwritten with the luminosity of the blank image. The threshold value can be previously determined by a preliminary experiment.

Alternatively, as another method of eliminating the influence of the fibroblast, the cancer cell and the fibroblast are distinguished depending on their shapes by image analysis as described in Patent Document 1, and information about only the cancer cell may be extracted.

The above treatment is repeated over the entire area of the sample, so that the influence of the noises not resulting from light absorption by the cancer cell can be eliminated.

Next, cancer cells are quantitated from the image from which the noises have been eliminated.

The cancer cell amount can be evaluated by integrating an indicator of the cell amount for each pixel. Preferably, the cancer cell amount is evaluated by an estimated volume value. This is because colonies of the cancer cells three-dimensionally develop by the collagen gel embedding cultivation, and thus their thicknesses can be taken into consideration for more accurate evaluation. The estimated volume value is obtained by determining an absorbance from the luminosity of each pixel and integrating the absorbance over the entire area of the sample. This is because the absorbance linearly correlates with the cell thickness in each region.

According to the Lambert-Beer law, if the intensity of the incident light to the sample is represented by $I_0$, and the intensity of the transmitted light is represented by 1, the following relationship is established;

$$I/I_0 = \exp(-\alpha L)$$

wherein, $\alpha$ represents an absorption coefficient of the stained cancer cell, and L represents a distance through which light passes in the cancer cell, i.e., a thickness of the cancer cell. An absorbance A by the cancer cell in each pixel is represented by the following equation:

$$\begin{aligned} A &= -\log(I/I_0) \\ &= (\alpha L)/2.303 \end{aligned}$$

and therefore the absorbance A is proportional to the thickness L of the cancer cell. The absorbance A is an indicator of the cell amount in the pixel, and the absorbance A is integrated over the entire area of the sample to determine the cell amount. Note that log is common logarithm.

On the other hand, from the corrected first image, the absorbance A is determined by the following equation:

$$A = \log\{(W-B)/(T_1-B)\}$$

wherein, W represents the luminosity of the pixel in the blank image, B represents the luminosity of the pixel in the dark image, and $T_1$ represents the luminosity of the pixel in the corrected first image.

Based on the above, the estimated volume value V of the cancer cell amount is determined by the following equation:

$$V = \Sigma L = C\Sigma A = C\Sigma[\log\{(W-B)/(T_1-B)\}] \quad \text{(Equation 1)}$$

wherein C is a constant. Thus, the absorbance is determined from the luminosity in each pixel, and the absorbance is integrated over the entire area of the sample to determine the estimated volume value of the cell.

Note that, when the luminosity $T_1$ of the pixel in the corrected first image equals to the luminosity B of the pixel in the dark image ($T_1=B$) for any reason, the denominator of the antilogarithm of the right-side logarithm in Equation 1 is 0, and thus calculation is impossible. In response to this, it is preferable that the luminosity etc. of the light source are adjusted so that the sample image is not too dark, and an exception handling suitable in the case of $T_1=B$ is carried out.

For simplicity, the luminosity of each pixel may be integrated to determine the absorbance from the integrated value. The estimated volume value $V_p$ is represented by the following equation:

$$V_p = C_p A_p = C_p \log\{(\Sigma W - \Sigma B)/(\Sigma T_1 - \Sigma B)\}$$

wherein, $C_p$ represents a constant, and $A_p$ represents an absorbance. In this equation, the absorbance is determined considering the entire area of the sample as one region, but if the cell amount is large, sufficient precision can be obtained e.g., in a case of using a surgical material as a starting material. Also when using this equation, the influence of noise due to dusts and the like has already been eliminated by the image processing.

In the anticancer agent susceptibility test, the susceptibility to the anticancer agent is evaluated by comparing the cancer cell amounts after cultivation between the control sample to which the anticancer agent has not been added and the sample to which the anticancer agent has been added.

The effect of the cancer cell-quantitating method of this embodiment will be described again.

Noises due to dusts and bubbles have been difficult to eliminate by conventional techniques. According to the method of the present embodiment, the first light and the second light are used to eliminate the influences of contamination of dust and remaining bubbles, so that the cancer cell can be precisely quantitated. Since opaque dusts are mis-recognized as cancer cells only with the first image and furthermore misrecognized as thick cancer cells because of dark shadow in the image, quantitative precision is significantly impaired. Also bubbles are misrecognized as cancer cells only with the first image, many of which are larger than colonies of cancer cells, and thus quantitative precision is significantly impaired.

Furthermore, the absorbance is determined and integrated for each of the divided regions in the sample image according to the above equation 1, so that the estimated volume value of the cancer cell can be calculated more precisely.

Next, a second embodiment of the cell measurement method of the present invention will be described.

This embodiment relates to a method for quantitating cancer cells in an anticancer agent susceptibility test as in the first embodiment. In the method of this embodiment, the method for taking the first image and the second image is different from that in the first embodiment. The other steps are the same as in the first embodiment.

In this embodiment, the first light source emitting the first light and the second light source emitting the second light are sequentially lighted, and one camera takes an image each time each light source is lighted. Thereby, the first image is obtained by imaging at the time of lighting the first light source, and the second image is obtained by imaging at the time of lighting the second light source. Also in this embodiment, the physical form of the light source is not particularly limited. For example, an LED chip as a first light source and an LED chip as a second light source may be incorporated in one LED package, or otherwise separate LED packages as a first light source and a second light source may be used and alternately arranged.

In this embodiment, a monochrome camera can be used. In that case, finer images can be obtained, because monochrome cameras with higher resolution are available than color cameras.

EXAMPLE

The first embodiment will be further specifically described with reference to Example.

A human colon cancer-derived cell line HCT-116 was used as a cancer cell, and cultured by a collagen gel embedding method. As a collagen gel solution for embedding the cell, 1 volume of a ten-time concentrated Ham's F12 medium (containing no sodium bicarbonate) and 1 volume of a buffer solution for reconstitution (50 mM-NaOH solution containing 260 mM of sodium bicarbonate and 200 mM of HEPES) were added to 8 volumes of Cell Matrix Type CD (KURABO INDUSTRIES LTD.), and stored in ice. The HCT-116 strain was added to the collagen solution so that its final density was $4 \times 10^4$ cells/mL, and mixed well to prepare a collagen mixture. 10 μL of this collagen mixture was dropped into each of three wells of a 24-well plate with appropriate intervals using a micro pipette. Thereafter, the mixture was warmed in a $CO_2$ incubator at 37° C. for 1 hour to prepare a collagen matrix containing the cancer cell. To the resulting collagen gel matrix, 1 mL of DF medium containing 10% FBS was added, and cultured for 16 hours. Then, an NR stain was injected into the wells, followed by formalin fixation and drying, to obtain a dried collagen gel.

The resulting dried collagen gel was placed on a sample stage and illuminated from below with an illumination, and a transmission image was imaged by a color camera. For the illumination, one LED package (MC-E Color, CREE Inc.) was used. RGB three-color LED chips were mounted in the LED package, and among them, only R chip and G chip were lighted for use. The first light was green light with a dominant wavelength of 528 nm, and the second light was red light with a dominant wavelength of 625 nm. For the color camera (XCL5005CR, Sony Corporation), the pixel number was 2448×2050, each of the RGB chips was constituted with 8-bit gradation, and a lens of 1.3 optical magnifications was used. At this time, the resolution of the image was about 2.7 μm.

Figure 6:
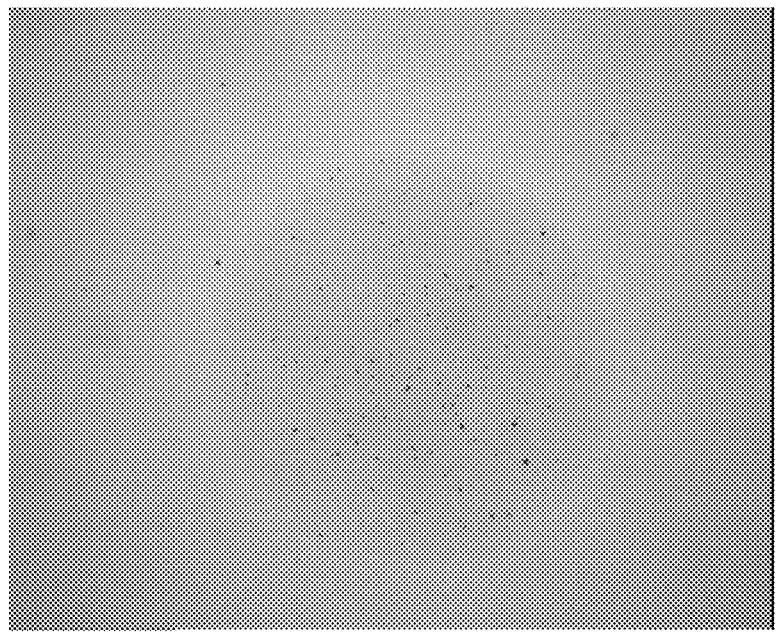
FIG. 6 is an original image of a sample in which a cancer cell was quantitated in Example.
Figure 7:
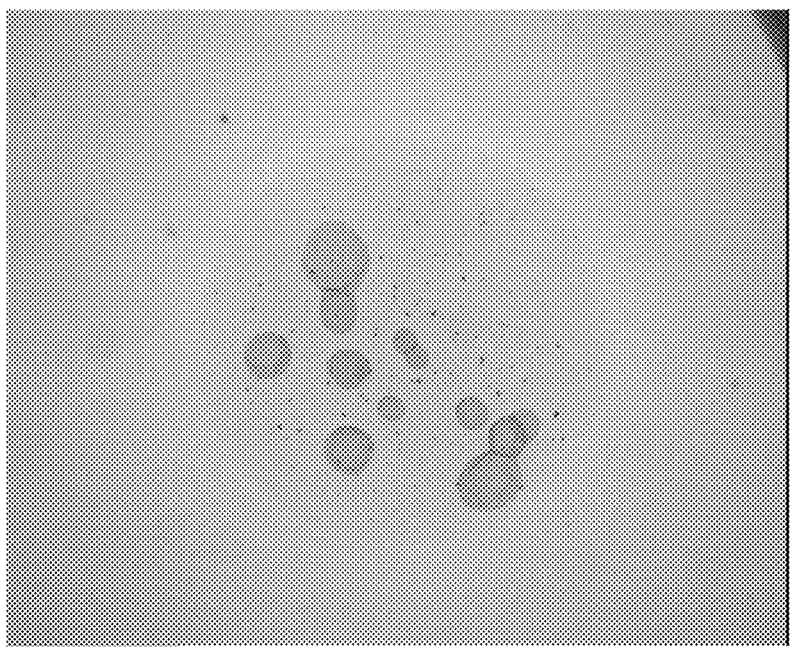
FIG. 7 is an original image of a sample in which a cancer cell was quantitated in Example.

In FIG. 6 (sample containing no bubble) and FIG. 7 (sample containing many bubbles), the imaged original images were converted into monochrome images. The samples shown in FIGS. 6 and 7 contain almost the same amount of cancer cell. Note that the above FIG. 4 also shows an image obtained by the same method as this Example. The original image was color-separated into three colors of RGB, and the G image was defined as a first image and the R image was defined as a second image. For each pixel, the first image and the second image were compared, and when a difference in luminosity was within 35, the pixel was judged to have no cancer cell. Absorbance was calculated for each pixel according to the above Equation 1, and integrated over the entire area of the sample to determine an estimated volume value of the cancer cell. At this time, a value of the constant C in Expression 1 was $2.0 \times 10^{-4}$.

As Comparative Example, the absorbance was calculated from the luminosity of the first image without using the second image, and similarly integrated over the entire area of the sample to determine an estimated volume value of the cancer cell.

The estimated volume values obtained by the method of Example were 0.42 in FIG. 6 and 0.44 in FIG. 7. In the method of Comparative Example, the estimated volume values were 0.47 in FIG. 6 and 1.54 in FIG. 7. In FIG. 6 without bubbles, Example and Comparative Example showed equivalent estimated volume values. On the other hand, in FIG. 7 with many bubbles, the estimated volume value according to Comparative Example was about three times that of Example. This was attributed to the influence of the noise due to the bubbles, and in Example, the noise due to the bubbles could be eliminated.

The cell measurement method of the present invention is not limited to the above-described Embodiments and Example, and can be variously modified within the scope of the technical idea of the invention.

For example, in the above-described Embodiment, relativization of the luminosity (blank correction), elimination of noises such as dusts and bubbles by comparison between the first image and the second image, and elimination of noises due to fibroblasts are carried out in this order, but their turns may be replaced.

In addition, images may be taken using e.g., a white illumination while sequentially switching color filters installed on the front of the camera, to obtain the first and second images.

In addition, images may be taken by a color camera using e.g., a white light source having continuous spectrum as an illumination, and color-separated to obtain the first and second images. However, since image sensor elements of the color camera generally have wide sensitivity spectra and partially overlap with each other, it had better use two light sources having different wavelengths for obtaining clear difference between the first and second images.

What is claimed is:

1. A cell measurement method, comprising:
    a step of staining a cultured target cell with a dye, wherein the target cell is a cell cultured by embedding the cell in a collagen gel;
    a step of obtaining a first image and a second image which are transmission images for a first light and a second light to which the dye has different absorbance;
    a step of dividing each of the first image and the second image into a plurality of divided regions and comparing the first image and the second image for each of the divided regions so as to eliminate noises; and
    a step of integrating an indicator of a cell amount in each of the divided regions in the images from which the noises were eliminated so as to evaluate a target cell amount.

2. The cell measurement method according to claim 1, wherein, in the step of eliminating the noises, the first image and the second image are compared for each of the divided regions, and when a difference or a ratio of luminosity between the divided regions subjected to the comparison is less than a predetermined value, the divided regions are excluded from the data as a basis for evaluation of the target cell amount.

3. The cell measurement method according to claim 1, wherein, the step of eliminating the noises, the first image and the second image are compared for each of the divided regions, and when a difference or a ratio of absorbance between the divided regions subjected to the comparison is less than a predetermined value, the divided regions are excluded from the data as a basis for evaluation of the target cell amount.

4. The cell measurement method according to claim 1, wherein the target cell is a cancer cell.

5. The cell measurement method according to claim 1, wherein the first image and the second image are obtained by color-separating an image taken using one color camera while concurrently applying the first light and the second light.

6. The cell measurement method according to claim 1, wherein the first image and the second image are obtained by independently taking each image using one camera while sequentially applying the first light and the second light.

7. The cell measurement method according to claim 1, wherein the target cell amount is evaluated by calculating an absorbance from an image luminosity for each of the divided regions, and integrating the obtained absorbance over the plurality of divided regions to calculate an estimated volume value of the target cell.

8. A cell measurement method, comprising:
   a step of staining a cultured target cell with a dye;
   a step of obtaining a first image and a second image which are transmission images for a first light and a second light to which the dye has different absorbance;
   a step of dividing each of the first image and the second image into a plurality of divided regions and comparing the first image and the second image for each of the divided regions so as to eliminate noises; and
   a step of integrating an indicator of a cell amount in each of the divided regions in the images from which the noises were eliminated so as to evaluate a target cell amount,
   wherein the target cell amount is evaluated by calculating an absorbance from an image luminosity for each of the divided regions, and integrating the obtained absorbance over the plurality of divided regions to calculate an estimated volume value of the target cell.

9. The cell measurement method according to claim 8, wherein, in the step of eliminating the noises, the first image and the second image are compared for each of the divided regions, and when a difference or a ratio of luminosity between the divided regions subjected to the comparison is less than a predetermined value, the divided regions are excluded from the data as a basis for evaluation of the target cell amount.

10. The cell measurement method according to claim 8, wherein, in the step of eliminating the noises, the first image and the second image are compared for each of the divided regions, and when a difference or a ratio of absorbance between the divided regions subjected to the comparison is less than a predetermined value, the divided regions are excluded from the data as a basis for evaluation of the target cell amount.

11. The cell measurement method according to claim 8, wherein the target cell is a cancer cell.

12. The cell measurement method according to claim 8, wherein, the first image and the second image are obtained by color-separating an image taken using one color camera while concurrently applying the first light and the second light.

13. The cell measurement method according to claim 8, wherein the first image and the second image are obtained by independently taking each image using one camera while sequentially applying the first light and the second light.

* * * * *